United States Patent
Goertz et al.

(10) Patent No.: US 7,256,000 B2
(45) Date of Patent: Aug. 14, 2007

(54) PREPARATION OF SPHERES FOR DIAGNOSTIC TESTS

(75) Inventors: Susan Goertz, Mississauga (CA); Paul Hemmes, Mississauga (CA)

(73) Assignee: Spectral Diagnostics, Ontario (CA)

( * ) Notice: Subject to any disclaimer, the term of this patent is extended or adjusted under 35 U.S.C. 154(b) by 958 days.

(21) Appl. No.: 10/190,213

(22) Filed: Jul. 5, 2002

(65) Prior Publication Data

US 2003/0059766 A1    Mar. 27, 2003

Related U.S. Application Data

(63) Continuation-in-part of application No. 09/353,191, filed on Jul. 14, 1999, now abandoned.

(51) Int. Cl.
*G01N 33/53* (2006.01)
(52) U.S. Cl. .................. 435/7.1; 424/417; 424/418; 424/450; 424/130.1; 424/134.1
(58) Field of Classification Search ............. 424/417, 424/418, 450, 130.1, 134.1; 435/7.1
See application file for complete search history.

(56) References Cited

U.S. PATENT DOCUMENTS

| | | |
|---|---|---|
| 3,721,725 A | 3/1973 | Briggs et al. |
| 3,932,943 A | 1/1976 | Briggs et al. |
| 4,115,537 A | 9/1978 | Driscoll et al. |
| 4,655,047 A | 4/1987 | Temple et al. |
| 4,678,812 A | 7/1987 | Bollin, Jr. et al. |
| 4,755,461 A | 7/1988 | Lawson et al. |
| 4,762,857 A | 8/1988 | Bollin, Jr. et al. |
| 4,820,627 A | 4/1989 | McGeehan |
| 4,848,094 A | 7/1989 | Davis et al. |
| 5,413,732 A | 5/1995 | Buhl et al. |
| 5,749,274 A | 5/1998 | Chiba |
| 5,776,563 A | 7/1998 | Buhl et al. |
| 5,804,370 A | 9/1998 | Romaschin et al. |

FOREIGN PATENT DOCUMENTS

EP    0410 207 A2    7/1990

*Primary Examiner*—Bao-Thuy L. Nguyen
(74) *Attorney, Agent, or Firm*—Klauber & Jackson

(57) ABSTRACT

The invention relates to surfactant-free reagent spheres useful for biological tests particularly those involving antigen/antibody reactions.

6 Claims, No Drawings

PREPARATION OF SPHERES FOR DIAGNOSTIC TESTS

CROSS-REFERENCE TO RELATED APPLICATION

This application is a continuation-in-part of Ser. No. 09/353,191, filed Jul. 14, 1999, now abandoned, incorporated herein by reference in its entirety.

TECHNICAL FIELD OF THE INVENTION

This invention relates to the production of stabilized beads or spheres which are detergent- or surfactant-free and contain diagnostically and therapeutically useful components such as antibodies, antigens, and other physiological agents useful for a variety of diagnostic and therapeutic purposes. It relates also to products produced by the novel processes.

BACKGROUND OF THE INVENTION

In preparing reagents for convenient and efficient testing of clinical biological samples, it is frequently important to obtain dry chemical blends in uniform, discrete amounts. Thus, reagents are normally precisely measured small, quantities of chemicals often with inert excipients. It has long been known that this is conveniently done by dispensing solutions of the chemicals. Unfortunately, liquid solutions of many materials, and in particular, biologically active materials such as antibodies, enzymes, certain proteins, and hydrolyzable materials are not generally stable in solution. Therefore reagents are often provided in dry form to improve stability.

Current technology for producing dry chemical blends involves procedures such as dry blending, spray drying, fluid bed drying and the formation of rigid spheres. All of these procedures, however, have limitations that make them costly, inefficient or difficult to implement. In dry blending technology, it is difficult to obtain homogeneous blends of chemicals that have different densities. Moreover, homogeneity is particularly difficult to achieve when very small amounts of ingredients are mixed with large amounts of others. Once made homogeneous, it is extremely difficult to reproducibly (within 1 percent) dispense small amounts (less than about 10 mg) of the blended chemicals.

Spray drying technology produces more homogeneous blends of chemicals because the reagents are first dissolved in liquid. Using spray drying, however, it is difficult and costly to obtain precisely sized amounts of blended chemicals. As generally practiced, this process yields particles with size distributions having coefficients of weight variation greater than 20 percent. The resulting particles have to be reprocessed to obtain uniform particle sizes. After agglomeration, the particles are generally less soluble than the original spray dried particles. Moreover, these procedures typically use halocarbons cryogenic solutions which are hazardous to the environment and cannot be employed with some reagents such as antibodies since they may inactivate them.

Fluid bed technology relies upon spraying a liquid reagent blend onto a particle and drying the liquid to obtain a particle coated with the blended reagents. Using this procedure, it is difficult to obtain uniformly sized particles and to produce a uniform product.

A commonly used alternative to production of the desired products is tube coating with a solution of the desired materials followed by heat, air or freeze-drying. Unfortunately, many materials that are tube coated bind strongly to the tube surface and will not rapidly redissolve when liquid is added to the tube. This can complicate assays due to the time lag required to achieve complete dissolution. In some cases, the slow and possibly incomplete redissolution will prevent the development of a useful assay.

It has now been discovered that the use of preformed uniform spheres, eliminates the slow dissolution problem and offers great advantages over tube drying techniques.

The preparation of rigid dry, substantially uniform spheres is an attractive alternative for producing dry blends since the spheres are relatively easy to prepare with defined quantities of ingredients, both active and inert. Additionally, they are easy to handle and dissolve readily in body fluids such as urine, blood, serum and plasma.

Heretofore such spheres or beads have been prepared from aqueous solutions containing detergents or surfactants by dropping measured quantities of the solutions into a cryogenic liquid such as nitrogen, collecting the frozen beads that form and thereafter, lyophilizing the beads to remove the moisture. The beads thus formed are useful for some purposes but cannot be employed in biological tests which are adversely affected by the presence of the residual surfactants which are distributed throughout the beads after lyophilization.

For example, the beads are not useful in tests which require whole blood or take place in the presence of intact red blood cells or intact white blood cells since the surfactants cause blood cell lysis and interfere with the test. This problem is especially acute if the test is one which requires visualization or detection of the product in the absence of quenching by hemoglobin, or intact white blood cells such as used in various chemiluminescent assays as described below.

The art has expended much time and effort seeking to produce dry, stable reagents containing exact quantities of selected components useful to analyze biological samples such as blood, plasma, serum, urine and other body fluids. See, for example the following U.S. Pat. Nos.: 3,721,725; 4,820,627; 3,932,943; 4,115,537 4,848,094; 4,755,461; 4,655,047; 4,678,812; and 4,762,857, which relate generally to dry blending spray drying and fluid bed drying.

A more recently issued patent, U.S. Pat. No. 5,413,732 describes and claims a method for providing lyophilized reagent spheres suitable for analysis of biological samples, in particular analysis of blood samples in a centrifugal analyzer.

A particular advantage of the process described is that the spheres are prepared from an aqueous solution. Hence there is no difficulty in insuring that in the final products the dry components are uniformly distributed and in the proper proportions.

The reagent spheres or beads preferred by the process of the patent are defined as comprising the reagents necessary for the proposed tests together with fillers and surfactants. See for example the first paragraph of column 1, column 6, lines 41 through 60 and all of the examples.

There are, as indicated above, biological tests which cannot be conducted in the presence of surfactants. One such test is a test for sepsis and infections described in *J. of Immunol. Methods* 212 (1996) 169-165; U.S. Pat. No. 5,804,370; U.S. patent application Ser. No. 06/991,230 filed Dec. 16, 1997, U.S. patent application Ser. No. 991,109 filed Dec. 16, 1997 and in U.S. patent application Ser. No. 353,189 filed Jul. 14, 1999. The inventions described in these publications are applicable to recognizing infections and sepsis, including its various stages. The crux of the inventions is the formation of an antibody/antigen complex which binds to specific receptors on neutrophils, lymphocytes or monocytes in the presence of complement to elicit an oxidative burst which can be detected as light emission using, for example, a chemiluminescent agent such as luminol or lucigenin. The level of the oxidative burst is related to the level of the antigen.

The tests are applicable to the recognition of a variety of antigens related to infection and sepsis including, for example, microorganisms and their components, including gram positive cell wall constituents and gram negative endotoxin, lipopolysaccharide, lipoteichoic acid, and the inflammatory mediators that appear in circulation as a result of the presence of these components including tumor necrosis factor (TNF), interleukin-1 (IL-1) and other interleukins and cytolcines. Other antigens to which the tests are applicable include those related to drugs of abuse, hormones, toxins, therapeutic drugs, markers of cardiac muscle damage, ovulation, pregnancy and other similar tests.

In accordance with the preferred procedure for conducting the tests, the complementary antibody to the antigen or analyte of interest is distributed in one or more spheres or beads such as those which are the subject matter of this invention.

It has been observed that if the spheres contain surfactants, they cannot be used to conduct the tests described since the surfactants interfere with the various reactions necessary to the production of a detectable and measurable light emission.

Still other tests which are not possible in the presence of surfactants is described in U.S. patent application Ser. No. 353,188 filed Jul. 14, 1999 and Ser. No. 353,190 filed Jul. 14, 1999. These tests also are based on antibody/antigen reactions which produce a detectable signal. While the tests are applicable to detecting a variety of antigens, they are particularly suitable to the detection of cardiac analytes such as myoglobin, troponin I, troponin T and CK-MB which are released into the blood from deteriorating cardiac tissue as a result of a tissue damaging event such as angina or myocardial infarction.

Briefly, the tests involve contacting a suspected sample of whole blood, plasma or serum with a detector antibody which is labeled with a detectable label. Gold is the preferred label since it produces a purple color which is visible to the naked eye. If there is a cardiac analyte complementary to the detector antibody present in the sample, the analyte and antibody will react to form a gold labeled antibody/analyte complex which then reacts with a capture antibody to concentrate the complex and increase the visibility of the purple color.

It is preferred to utilize whole blood for conducting the tests rather than either serum or plasma. However, the red blood cells in whole blood interfere with the visual detection of the color produced by the selected label.

The above identified patent applications describe a device for the rapid detection of cardiac analytes using whole blood. Briefly, the device is a hand held device in which a porous membrane is held between upper and lower rigid supports. The membrane is typically nitrocellulose. The supports are plastic such as an acrylic polymer. The supports, may be transparent to permit the user to see the color formed as a result of the reactions taking place. Alternatively, they may be opaque with an opening through which the delectable signal may be observed.

The device is formed with a pathway for the movement of a test sample from the entry port to the capture antibody. The pathway includes channels formed in the support members which are in cooperative contact with other channels formed in the porous membrane.

In one embodiment of the inventions described in the applications, whole blood enters the pathway and passes around a bead containing a labeled detector antibody, dissolves the bead and its components and then flows onto the porous membrane. The whole blood moves through the membrane by capillary action. As it passes through the membrane the red cells are chromatographically separated from the plasma. The plasma then enters a channel in the membrane where the capture antibody is located.

In a positive test utilizing a gold label, the bead containing the antibody dissolves in the whole blood and the labeled antibody/analyte complex forms. The red blood cells are separated as described and the plasma containing the complex, but free of red blood cells, enters the capture channel where the complex reacts with the capture antibody.

The device may be designed with one or more capture channels to detect one or several analytes. If only one capture channel is used, it may contain one or more spaced capture antibodies. Alternatively, there may be one capture antibody in each of two or more capture channels. Thus, the device may be employed to detect each of the analytes mentioned above or any combination of them. It is, of course not limited to the analytes mentioned but may with appropriate complementary antibodies, either monoclonal or polyclonal, be used to detect any of the large number of analytes known to be released by damaged cardiac tissue. Many such analytes are identified in U.S. Pat. No. 5,749,274 issued on May 5, 1998.

As with the sepsis and infection tests mentioned above, the presence of surfactants in the antibody containing bead interferes with the tests for analyzing whole blood for cardiac analytes. In this case, the interference arises because the surfactants cause hemolysis of the red blood cells releasing all of their components including the richly colored hemoglobin. The hemoglobin cannot be separated by the membrane and, as a result, enters the capture channel and obscures the signal.

SUMMARY OF THE INVENTION

This invention provides lyophilized, rigid, surfactant-free reagents spheres containing at least one reagent in a carbohydrate lattice. The spheres are useful for analyzing bodily fluids for the presence of analytes, including those which serve as diagnostically-useful markers of a medical condition. The spheres of the present invention are especially useful in the performance of bioassays with samples containing cells that are, and must retain, intact, to prevent assay contamination and/or to retain analyte integrity. In specific embodiments of the invention, the reagent is an antibody reactive with a diagnostic marker of a given medical condition.

Accordingly, in one aspect of the present invention, there is provided a lyophilized, rigid, surfactant-free reagent sphere containing at least one reagent in a carbohydrate lattice. In embodiments of the invention, the beads are generally uniform in size, by virtue of having been formed from droplets of generally uniform volume.

In preferred embodiments of the present invention, the spheres contain a reagent that is a binding partner for the analyte of interest, and most preferably is an antibody. Particularly preferred reagents are antibodies reactive with a marker that is diagnostic of a given medical condition.

In another aspect of the present invention, the spheres are provided specifically for use in performing a bioassay on a sample containing intact cells. Such samples include, for instance, whole blood and cell-containing fractions thereof. Thus, the present invention further provides a method for performing a bioassay on a sample containing intact cells, the method comprising the step of obtaining one or more surfactant-free spheres of the present invention which contain a reagent useful in the detection of an analyte present in the sample, incubating the spheres with the sample containing intact cells, and then determining the presence of the analyte reactive with the reagent.

In another aspect of the present invention, there is provided a process for preparing the spheres of the present invention, comprising the steps of:
  (a) forming an aqueous solution comprising a reagent and a carbohydrate useful in the preparation of reagent spheres, the aqueous solution being essentially free from surfactant capable of lysing intact cells during performance of a bioassay;
  (b) dispensing the aqueous solution as discrete drops of substantially uniform volume into a cryogenic solution;
  (c) maintaining the drops in the cryogenic solution to cause freezing thereof; and
  (d) lyophilizing the frozen drops to form dry, surfactant-free reagent spheres.

Drop weighing of liquids is an established method for ensuring the production of drops of uniform size. Uniform size results from the production of drops having uniform surface tension resulting from the use of surfactants. In the absence of surfactants, there may be variation in the surface tension of the drops and this results in the production of drops which lack uniformity due to impurities, such as dust or chemicals in the liquid phase.

In the light of the teachings of the prior art, it is surprising to find that useful spheres can be produced from solutions which do not contain surfactants. These surprising findings not only reduce the costs of production but also extend the utility of the spheres to tests and assays in which the presence of surfactants is detrimental. The terms surfactant and detergent are used interchangeably herein.

The spheres of this invention retain all of the art-recognized advantages of the earlier products containing surfactants. They dissolve rapidly, are easy to handle and are sufficiently rigid so that they are not easily crushed or otherwise damaged by rough treatment. Additionally, because they are prepared from solutions, their components, even those present in small amounts, are uniformly distributed.

DETAILED DESCRIPTION OF THE INVENTION

The spheres of the present invention are characterized as lyophilized, rigid, reagent spheres that are essentially free from surfactant. Spheres that are essentially free from surfactant have the benefit that they do not interfere with cell-based bioassays by causing or promoting cell lysis. Accordingly, spheres that are essentially free from surfactant are spheres that, when mixed with a cell-bearing sample, do not cause or promote any unwanted lysis of cells in the sample.

The spheres of the present invention contain an inert, water-soluble carbohydrate that serves to form a lattice structure that gives the spheres, in their lyophilized form, a rigidity that, on the one hand, confers stability during handling and, on the other hand, allows them to dissolve rapidly in an aqueous reaction medium. Carbohydrates useful in preparing such spheres are known in the art, and include mannitol, maltose, lactose, inositol, dextran and trehalose. Trehalose is especially preferred because it allows the preparation of excellent products and because of its known stabilizing properties.

In addition to the carbohydrate, the spheres of the present invention contain a reagent useful to assay a given analyte. A wide variety of such reagents are useful in, and contemplated by, the present invention. Because the spheres of the present invention are well-adapted for use in cell-based assays, they are well suited to incorporate one or more reagents of a type useful in bioassays. Such reagents include antigens, antibodies, and various other markers of medical conditions, disorders and diseases which may be proteins, nucleic acids and carbohydrates. In certain embodiments, the spheres contain one or more reagents for performing a particular assay for a particular analyte, which may include, for example, a substrate on which the analyte may act, an enzyme which acts on the analyte or on the product of a previous enzymatic reaction, a co-factor for an enzyme, a chromogenic reagent to form a visibly-detectable product, a fluorogenic reagent to form a fluorescent product, a chemiluminescent reagent to form a product detectable by luminescence, or a specific nucleic acid probe such as a molecular beacon. Reagent spheres may contain a particular combination of reagents for determining one analyte, or a plurality of such reagent combinations for determining more than one analyte in a sample. Reagent spheres may contain a calibrator, standard or positive control reagent for a particular assay. These examples are merely exemplary and non-limiting as to the various uses by which the reagents spheres of the invention may be employed to provide reagents determinative of one or more analytes, particularly in systems sensitive to the presence of detergents or surfactants.

In a preferred embodiment of the invention, the reagent is an antibody reactive with an analyte of diagnostic interest or with a therapeutic target of interest. Such antibodies may be reactive with such analytes as markers of disease or medical conditions. In one embodiment, the antibody is an IgM antibody reactive with lipopolysaccharide (LPS) which is a marker of sepsis. In other embodiments, the antibody is reactive with markers of disease progression. For instance, proteins elicited in cascade fashion can be detected when the antibody is reactive with these proteins. In the case of sepsis, the antibodies can be reactive with TNF, IL-6 and other interleukins and cytokines produced in response to an initial mediator of the sepsis cascade. Alternatively, the antibody can be one reactive with markers of cardiac damage, e.g., with troponin I, creatine kinase MB, myoglobin and the like, for instance to diagnose myocardial infarct. It is not intended to be limited to the type of antibody nor to the species of antibody incorporated within the spheres. It is also to be appreciated that a given sphere may incorporate a number of antibodies reactive with different antigens.

In addition to carbohydrate and analyte, e.g., antibody, the spheres of the present invention may further contain fillers and other carriers commonly used in sphere preparation, other than surfactants or detergents.

To prepare the products of this invention, the first step is to dissolve the components in water to form an aqueous solution comprising the selected carbohydrate and antibody at the proper concentration.

The solution is preferably, although not necessarily, degassed and then added dropwise to liquid nitrogen in a container such as a Dewar flask. The drops may be formed by spraying through a needle with a selected orifice. Preferably, however the drops are dispensed through a pump calibrated so that the drops each are of a uniform volume. The distance through which the drops fall is sufficient so that they form uniform spheres. When the spheres reach the cold liquid nitrogen vapor they begin to freeze while suspended in a layer of vapor. When freezing is complete (about 10-20 sec.), the spheres sink to the bottom of the liquid nitrogen while retaining their spherical shape.

It is important that the time interval between the release of the drops from the pump or needle orifice is such that they do not collide with each other before they are frozen. Otherwise the formed products will not be of uniform size, shape and volume.

Liquid nitrogen is the refrigerant of choice for the practice of this invention because it is readily available and easy to handle. Additionally, it is inert to the components of the beads, especially the antibodies which other refrigerants such as halohydrocarbons may deactivate.

Once the spheres are formed, they are ready for lyophilization. This step should be performed without allowing the spheres to thaw. If they thaw, they will simply run together and reform the aqueous solution. Accordingly, the beads desirably are not collected from the nitrogen but instead are retained under the nitrogen.

One safe procedure for accomplishing lyophilization is to transfer the liquid nitrogen and the beads to a pan or other broad shallow container for example one of stainless steel. Some of the nitrogen may be permitted to evaporate. However, sufficient nitrogen must remain in the pan so that the spheres are under nitrogen and frozen.

At the appropriate time, the pan is transferred to a lyophilizer which has been precooled to about $-20°$ C. to $-30°$ C. and the freeze drying cycle is initiated.

The rate of lyophilization may be incrementally increased to make the process more efficient and to increase the rate at which the dry spheres are obtained.

Wide variations in freeze drying cycles are possible without adverse effect. A typical cycle is:12 to 18 hours at $-20°$ C. to $-15°$ C.; 1 to 4 hours at $-10°$ C. to $10°$ C.; 1 to 4 hours at $20°$ C. to $25°$ C.

The optimum cycle will, of course, depend on several factors including the quantity of spheres produced, the desired rate of production, the size and surface area of the beads and the ability of the antibody to withstand the rigors of the lyophilization process.

Once the freeze drying cycle is completed, the spheres are collected and either used immediately or placed in a container or desiccator where they are protected from moisture. Beads prepared in this manner have been found to maintain their stability and ability of the contained antibody or antibodies to bond with their complementary antigen for as long as two months at ambient temperature.

The products produced by the process of this invention are uniform spheres comprising a carbohydrate lattice in which in one embodiment, a preselected quantity of one or more antibodies is distributed. The amount of a particular antibody in the sphere is selected so that when the sphere dissolves in the bodily sample to be analyzed the concentration of the antibody will be at the appropriate level to react with the antigen. It will depend upon several factors well known to the skilled artisan or readily ascertainable by known procedures. These factors include, for example, the test being performed, the expected concentration of the antigen and the affinity of the antibody for the antigen.

The process of this invention is applicable to the production of spheres in which the amount of antibody present is at substantially any, practical value for the performance of known assays.

The process may be utilized to prepare spheres of any desired practical size or volume useful to conduct biological assays.

The teachings of the patents and applications referred to in this disclosure are, by such reference, included herein in their entirety.

The following examples are given by way of illustration only and are not to be considered limitations of this invention since many apparent variations are possible without varying from the spirit or scope thereof.

EXAMPLE 1

1. IgM Antibody Beads

For this batch of antibody beads, 1200 beads were produced at a concentration of 0.5 microgram/20 microliter bead.

A vial of IgM antibody, at a concentration of 1.18 mg/ml, was removed from the $-20°$ C. freezer, thawed and vortexed. The matrix used to dilute the antibody was 0.3M trehalose, prepared in sterile endotoxin-free water and 0.2 micrometer filtered.

The total volume required was: 1200 beads×20 microliter/bead=24000 microliter=24 ml. The amount of IgM required was: 1200 beads×0.5 microgram/bead=600 microgram=0.6 mg. The volume of IgM antibody required was: 0.6 mg/1.18 mg/ml=0.508 ml=508 microliter. The volume of 0.3M trehalose required was: 24 ml–0.508 ml=23.492 ml.

The IgM and the trehalose were mixed together in a 50 ml sterile conical tube and vortexed. The solution was then put on ice to keep the solution cold.

The IgM dedicated dual pump module was cleaned using bleach and sodium hydroxide, and then rinsed with autoclaved water. The pump module A was calibrated to 20.1 microliter and pump module B was calibrated to 20.0 microliter using autoclaved water. Once the dual pump module was calibrated, both inlet lines to the pump modules were placed into the 50 ml conical tube containing the IgM solution and the solution was primed through the pump lines ready for dispensing.

The weights of the IgM drops were measured by dispensing a single drop into 5 pre-weighed centrifuge tubes, and the tubes were re-weighed. This was done for each pump module to ensure the pump modules were correctly calibrated. The correct calibration weight for the IgM antibody drop is between 20.3 to 20.8 mg.

| Beads # | Pump Module A | Pump Module B |
|---------|---------------|---------------|
| 1 | 20.4 | 21.0 |
| 2 | 20.5 | 20.8 |
| 3 | 20.5 | 20.9 |
| 4 | 20.2 | 21.0 |
| 5 | 20.4 | 21.4 |
| Mean, mg | 20.4 | 21.02 |
| SD, mg | 0.12 | 0.23 |
| % CV | 0.6% | 1.1% |

Pump module A was correctly calibrated but pump module B had drifted during priming of the lines; therefore, it was re-calibrated to 20.5 mg.

| Beads # | Pump Module A | Pump Module B |
|---|---|---|
| 1 | 20.5 | 20.5 |
| 2 | 20.5 | 20.9 |
| 3 | 20.5 | 20.6 |
| 4 | 20.5 | 20.4 |
| 5 | 20.6 | 20.5 |
| Mean, mg | 20.52 | 20.58 |
| SD, mg | 0.04 | 0.19 |
| % CV | 0.2% | 0.9% |

Liquid nitrogen was poured into two Dewars and placed directly below the dispensing tips. The tip was approximately 5 cm above the edge of the Dewar to avoid freezing. The automatic timer was started and every 6 seconds two drops were dispensed, one into each Dewar. When the entire IgM solution volume had been dispensed, both Dewars were emptied (liquid nitrogen and beads) into a baked stainless steel tray.

The tray was placed into a pre-chilled (−20° C.) lyophilizer for freeze-drying, The freeze drying cycle was: 12 hours at −20° C.; 1 hour at 0° C.; 1 hour at 25° C. After the freeze drying cycle had finished, the beads were removed from the lyophilizer and poured into a 50 ml sterile conical tube and labeled. The beads were then tested and showed good activity and precision.

2. LPS (Lipopolysaccharide) Beads

For this batch of LPS beads, 6000 beads were produced at a concentration of 2 ng/20 microliter per bead.

A vial of LPS stock at a Concentration of 1 mg/ml, was removed from the −20° C. freezer, thawed and vortexed thoroughly. The matrix used to dilute the antibody was 0.3M trehalose, prepared in sterile endotoxin-free water and 0.2 micrometer filtered. A 1/1000 dilution of the LPS was prepared to produce a 1 microgram/ml concentration. 20 microliter of the LPS stock was mixed with 20 ml of 0.3M trehalose in a 20 ml baked glass bottle with autoclaved polypropylene lid and vortexed thoroughly.

The total volume required was: 6000 beads×20 microliter/bead=120000 microliter=120 ml. The amount of LPS required was: 6000 beads×2 ng/bead=12000 ng=12 microgram. The volume of LPS required was: 12 microgram/1 microgram/ml=12 ml. The volume of 0.3M trehalose required was: 120 ml−12 ml=108 ml.

The 108 ml of 0.3M trehalose was degassed first, then mixed with the LPS in a 300 ml baked beaker and stirred (the stir bar was autoclaved). The solution was then aliquotted, in 24 ml volumes, into 6-30 ml baked glass bottles and frozen at −20° C. This was done because LPS in dilute solution is not stable at 4° C. for long periods of time.

The LPS dedicated pump module was cleaned using bleach and sodium hydroxide, and then rinsed with autoclaved water. The pump module was calibrated to 20.0 microliter using autoclaved water. Once the pump module was calibrated, the first bottle of the LPS solution was removed from the freezer, thawed, vortexed, degassed and then put on ice to keep the solution cold. The inlet line to the pump module was placed into the bottle containing the LPS solution and the solution was primed through the pump lines ready for dispensing. Every two hours (or when needed) a bottle was removed from the freezer thawed, vortex thoroughly and degassed before being pipetted into the dispensing bottle.

The weights of the LPS drops were measured by dispensing a single drop into 5 pre-weighed centrifuge tubes, and the tubes were re-weighed. This was done to ensure the pump module was corrected calibrated The correct calibration weight for the LPS drop is between 20.3 to 20.8 mg.

| Beads # | Pump Module |
|---|---|
| 1 | 20.5 |
| 2 | 20.5 |
| 3 | 20.6 |
| 4 | 20.4 |
| 5 | 20.3 |
| Mean, mg | 20.46 |
| SD, mg | 0.11 |
| % CV | 0.6% |

Liquid nitrogen was poured into a Dewar and placed directly below the dispensing tip. The tip was approximately 5 cm above the edge of the Dewar to avoid freezing. The automatic timer was started and every 6 seconds a drop was dispensed into the Dewar. When the entire LPS solution volume had been dispensed, the Dewar was emptied (liquid nitrogen and beads) into a baked stainless steel tray.

The tray was placed into a pre-chilled (−20° C.) lyophilizer for freeze-drying. The freeze drying cycle was: 12 hours at −20° C.; 1 hour at 0° C.; 1 hour at 25° C. After the freeze drying cycle had finished, the beads were removed from the lyophilizer and poured into 4-50 ml sterile conical tubes and labeled. The beads were then tested and showed good activity and precision.

3. Zymosan Beads

Zymosan is a particulate suspension that has to be kept stirring to keep the particles in suspension. If the solution is left to stand the zymosan will settle to the bottom of the tube. For this batch of zymosan beads, 450 beads were produced at 20 microliter per bead.

When the zymosan was made it was made to a final concentration of 3 mg/ml in sterile saline and stored frozen in 50 ml sterile conical tubes. Therefore the zymosan needed to be washed with autoclave water to remove the saline. First the required volume of zymosan needed to be calculated.

The volume of zymosan required was 450 beads×20 microliter/bead=9000 microliter=9 ml.

Nine mls of zymosan was thawed, vortexed and then centrifuged at 1500 rpm for 10 minutes. The supernatant was aspirated and the pellet resuspended to the original volume with autoclaved water and vortexed. The zymosan was again, spun down, supernatant aspirated and the pellet resuspended with autoclaved water.

The zymosan was centrifuged one last time at 1500 rpm for 10 minutes. The supernatant was aspirated but this time the pellet was resuspended to its original volume of 9 mls with 0.3M trehalose, prepared in sterile endotoxin-free water and 0.2 micrometer filtered.

The pump module was cleaned using bleach and sodium hydroxide, and then rinsed with autoclaved water. The pump module was calibrated to 20.0 microliter using autoclaved water.

Once the pump module was calibrated, the inlet line to the pump module was placed into the tube containing the zymosan solution and the solution was primed through the pump lines ready for dispensing.

Liquid nitrogen was poured into a Dewar and placed directly below the dispensing tip. The tip was approximately 5 cm above the edge of the Dewar to avoid freezing. The automatic timer was started and every 6 seconds a drop was dispensed into the Dewar. When the entire zymosan suspension volume had been dispensed, the Dewar was emptied (liquid nitrogen and beads) into a baked stainless steel tray.

The tray was placed into a pre-chilled (−20° C.) lyophilizer for freeze-drying. The freeze drying cycle was: 12 hours at −20° C.; 1 hour at 0° C.; 1 hour at 25° C. After the freeze drying cycle had finished, the beads were removed from the lyophilizer and poured into a 50 ml sterile conical tubes and labeled.

These beads were used to test for sepsis in accordance with the procedures described in the patent and patent applications identified above.

EXAMPLE 2

The same procedures were used to prepare spheres containing antibodies for troponin I, CK-MB, myoglobin and other cardiac analytes including combinations of analytes, antibodies which react with gram positive and gram negative bacteria, lipoteichoic acid, tumor necrosis factor, interleukins and other products.

EXAMPLE 3

The above-described IgM anti-LPS antibody beads and LPS beads were used to measure the amount of endotoxin (LPS) in a sample of whole blood using a three-tube assay as described in co-pending application Ser. No. 09/353,189. This assay takes advantage of white blood cells present in the whole blood sample to produce oxidants at a level proportional to the level of immunocomplexes formed in the sample between the added anti-LPS antibody and any LPS present in the sample. Zymosan enhances oxidant output. Luminol converts oxidants to visible light output, measured in a luminometer. The assay is performed in the absence of detergents or surfactants, as the white blood cells in the sample must remain intact for the generation of oxidants in proportion to the level of immunocomplexes; red blood cells must remain intact to avoid interference in the measurement of oxidants. The following reaction aliquots were prepared:

A=Whole blood+zymosan
B=Whole blood+zymosan+anti-LPS antibody
C=Whole blood+zymosan+anti-LPS antibody+exogenous LPS Blood samples used for the assay were drawn by venipuncture or through indwelling arterial lines into sterile 3 ml EDTA anti-coagulated Vacutainer tubes (Becton Dickenson, Franklin Lakes, N.J.) which were pretested for LPS content (less than 0.005 EU/ml).

The buffer for measurement of whole blood or white cell chemiluminescence studies was HBSS (pyrogen free, endotoxin less than 0.005 EU/ml) containing 1.5 mM calcium salt and 0.9 mM magnesium salt (Gibco BRL, Grand Island, N.Y.). This buffer (500 ml) was vigorously mixed overnight at 25 C. with luminol to yield a saturated solution (150 µM, HBSS-luminol) and then supplemented with 4 U/ml of lithium heparin and zymosan.

All chemiluminescence experiments were assayed in triplicate and the results expressed as the mean luminometer counts per minute±1 SD. Assays may also be prepared using duplicate or single tubes for reaction tubes A, B and C.

The following assay protocol was followed. Two aliquots of blood (500 µl) are dispensed into depyrogenated glass tubes into a thermostatted aluminum block pre-heated to 37 C. One tube contained a maximal dose of LPS (2.3 ng, in one 20 µl bead); the other tube is empty. These tubes are incubated for 10 min. at 37 C. During the last 5 minutes of this incubation glass or polystyrene assay tubes are loaded into the heating block. Three tubes are used per assay. Tube A contains control reagent used for antibody stabilization or no reagent at all; tubes B and C contain antibody (two beads per tube, 0.75 µg IgM per bead). To each tube a mixture of Luminol Buffer with unopsonized zymosan is added (500 µl per tube). This mixture is temperature equilibrated for at least 5 min. After the blood has incubated for a total of 10 min. at 37 C., 40 µl is transferred into each of assay tubes A and B from the blood tube with no LPS and 20 µl is transferred from the blood tube containing LPS into assay tube C. All tubes are vortexed and placed in the chemiluminometer for reading. The luminometer is thermostatted at 37 C. and the assay is read for a total of 20 min.

The 20-minute light integrals of tubes A, B and C are used to calculate the amount of LPS in the sample as follows. The amount of LPS present in the sample is referred to as "endotoxin activity" (EA), and calculate from the light integrals as follows:

$$EA = 100 \times \frac{\text{Light Integral Tube } B - \text{Light Integral Tube } A}{\text{Light Integral Tube } C - \text{Light Integral Tube } A}.$$

In this manner the EA is calculated and the decision of whether a patient is endotoxemic or not may be based on a cutoff value of range, i.e.>40 units EA, an indicator of of clinically significant endotoxemia. Gram negative infection may be ruled out for samples with results less than or equal to 0.4 EA units.

Further parameters are available from the three-tube assay results as pertains to the stage of sepsis. Responsiveness (R) of the patients white blood cells, a measure of the maximal ability of the white blood cell to bind and respond to opsonized immunocomplexes as defined above, is calculated as follows:

$$R = 1 - \frac{\text{Light Integral Tube } A}{\text{Light Integral Tube } C}.$$

Furthermore, a measure of the level of white blood cell activation and cell number (CLmax) may be measured as the peak luminometer count rate of tube A during the course of the assay. The maximum oxidant production of neutrophils, as measured by CLmax, is a measure of the ability of the white blood cell to respond to programmed opsonic challenge.

Although the surfactant-free reagent spheres of this invention are especially useful for conducting tests and analysis of bodily fluids in which surfactants have a damaging effect, the skilled artisan will recognize that they may also be employed in conventional tests based on antigenlantibody or other types of reactions, including enzymatic, chromogenic, fluorogenic reactions, or reactions employing a combinations of the foregoing. Typical tests and assays in which the spheres of this invention may be utilized include glucose, lactate dehydrogenase, serum glutamic-oxaloacetic transaminase (SGOT), serum glutamic pyruvic transaminase (SGPT), blood urea nitrogen (BUN), total protein, alkalinity, alkaline phosphatase, creatine protein bilirubin, calcium, chloride, sodium, potassium, magnesium, and the like. This list is not exhaustive and is intended merely as being exemplary of the assays which may be performed with the surfactant-free spheres of the present invention.

What is claimed is:

1. A lyophilized, rigid, surfactant-free reagent sphere useful to determine the presence of one or more antigens in a bodily fluid, said sphere prepared by freezing in liquid nitrogen and comprising at least one antibody reactive with the antigen, wherein said antibody is distributed throughout a carbohydrate lattice.

2. The reagent sphere of claim 1 wherein the carbohydrate is trehalose.

3. The reagent sphere of claim 1 wherein the antibody reacts with an antigen indicative of sepsis.

4. The reagent sphere of claim 3 wherein the antibody reacts with lipoteichoic acid, teichoic acid or a peptidoglycan.

5. The reagent sphere of claim 3 wherein the antibody reacts with lipopolysaccharide.

6. A method for performing a bioassay requiring detection of an analyte borne in a sample containing intact cells, the method comprising the steps of obtaining a lyophilized, rigid reagent sphere according to claim 1, incubating the reagent sphere with the sample, and determining the presence of the analyte.

* * * * *